(12) United States Patent
Lou et al.

(10) Patent No.: US 11,969,239 B2
(45) Date of Patent: Apr. 30, 2024

(54) TUMOR TISSUE CHARACTERIZATION USING MULTI-PARAMETRIC MAGNETIC RESONANCE IMAGING

(71) Applicant: Siemens Healthcare GmbH, Erlangen (DE)

(72) Inventors: Bin Lou, Princeton, NJ (US); Benjamin L. Odry, West New York, NJ (US)

(73) Assignee: Siemens Healthineers AG, Forchheim (DE)

( * ) Notice: Subject to any disclaimer, the term of this patent is extended or adjusted under 35 U.S.C. 154(b) by 174 days.

(21) Appl. No.: 16/743,418

(22) Filed: Jan. 15, 2020

(65) Prior Publication Data
US 2020/0275857 A1 Sep. 3, 2020

Related U.S. Application Data

(60) Provisional application No. 62/812,385, filed on Mar. 1, 2019.

(51) Int. Cl.
*A61B 5/055* (2006.01)
*G01R 33/46* (2006.01)
(Continued)

(52) U.S. Cl.
CPC ............... *A61B 5/055* (2013.01); *G01R 33/46* (2013.01); *G01R 33/50* (2013.01);
(Continued)

(58) Field of Classification Search
CPC ........ A61B 5/055; G01R 33/46; G01R 33/50; G01R 33/56341; G01R 33/34084;
(Continued)

(56) References Cited

U.S. PATENT DOCUMENTS

2010/0027865 A1  2/2010  Wels et al.
2010/0329529 A1*  12/2010  Feldman ........... G06F 18/21375
                                                                382/131
(Continued)

FOREIGN PATENT DOCUMENTS

CN    107330267 A  * 11/2017  ............... G06T 7/32
CN    107492090 A    12/2017
(Continued)

OTHER PUBLICATIONS

Huan et al., "Weakly Supervised Learning of Placental Ultrasound Images with Residual Networks", published Jul. 11-13, 2017, Proceeding in Medical Imaging (Year: 2017).*

(Continued)

*Primary Examiner* — Shahdeep Mohammed
*Assistant Examiner* — Fikirte (Fiki) T Ashine (57) ABSTRACT

Brain tumor or other tissue classification and/or segmentation is provided based on from multi-parametric MRI. MRI spectroscopy, such as in combination with structural and/or diffusion MRI measurements, are used to classify. A machine-learned model or classifier distinguishes between the types of tissue in response to input of the multi-parametric MRI. To deal with limited training data for tumors, a patch-based system may be used. To better assist physicians in interpreting results, a confidence map may be generated using the machine-learned classifier.

14 Claims, 4 Drawing Sheets

(51) Int. Cl.
*G01R 33/50* (2006.01)
*G01R 33/563* (2006.01)
*G06T 7/00* (2017.01)
*G01R 33/34* (2006.01)

(52) U.S. Cl.
CPC ...... *G01R 33/56341* (2013.01); *G06T 7/0012* (2013.01); *G01R 33/34084* (2013.01)

(58) Field of Classification Search
CPC ............. G06T 7/11; G06T 2207/10088; G06T 2207/20084; G06T 2207/30016; G06T 7/174; G06T 7/0012; G06T 2207/20081; G06T 2207/30096; G06K 9/6268; G06N 3/0454; G06N 3/08
See application file for complete search history.

(56) References Cited

U.S. PATENT DOCUMENTS

| | | | |
|---|---|---|---|
| 2014/0037172 | A1 | 2/2014 | Madabhushi et al. |
| 2015/0254493 | A1 | 9/2015 | Madabhushi et al. |
| 2016/0174902 | A1* | 6/2016 | Georgescu ............. G06V 10/82 600/408 |
| 2017/0176565 | A1 | 6/2017 | Kwak et al. |
| 2018/0055408 | A1 | 3/2018 | Song et al. |
| 2019/0130074 | A1* | 5/2019 | Itu ......................... G06K 9/6267 |
| 2019/0304092 | A1* | 10/2019 | Akselrod-Ballin .... G06N 3/084 |

FOREIGN PATENT DOCUMENTS

| | | | | |
|---|---|---|---|---|
| CN | 107851194 | A | | 3/2018 |
| CN | 108229343 | A | | 6/2018 |
| CN | 108492297 | A | * 9/2018 | ........... G06N 3/0454 |
| CN | 108876836 | A | | 11/2018 |
| CN | 108961274 | A | | 12/2018 |
| CN | 109117760 | A | | 1/2019 |
| CN | 109242866 | A | | 1/2019 |
| CN | 109259806 | A | | 1/2019 |
| FR | 3013847 | A1 | | 5/2015 |
| WO | 2010115885 | A1 | | 10/2010 |
| WO | 2013185087 | A1 | | 12/2013 |
| WO | 2014174317 | A2 | | 10/2014 |
| WO | 2015040434 | A1 | | 3/2015 |

OTHER PUBLICATIONS

M. Fraz et al., "Uncertainty Driven Pooling Network for Microvessel Segmentation in Routine Histology Images "published on Aug. 2018 (Year: 2018).*

Wagarachchi et al., "Optimization of Multi-layer Artificial Neural Networks Using Delta Values of Hidden Layers" published in 2013 IEEE. (Year: 2013).*

Fraz et al., "Uncertainty Driven Pooling Network for Microvessel Segmentation in Routine Histology Images" (Year: 2018).*

Al-Okaili, Riyadh N., et al. "Advanced MR imaging techniques in the diagnosis of intraaxial brain tumors in adults." Radiographics 26.suppl_1 (2006): S173-S189.

Ghesu, Florin-Cristian, et al. "Multi-scale deep reinforcement learning for real-time 3D-landmark detection in CT scans." IEEE transactions on pattern analysis and machine intelligence 41.1 (2017): 176-189.

European Search Report in EP application No. 23199980.6 dated Jan. 22, 2024, 10 pages.

Lemaitre, Guillaume, et al. "Computer-aided detection for prostate cancer detection based on multi-parametric magnetic resonance imaging." 2017 39th Annual International Conference of the IEEE Engineering in Medicine and Biology Society (EMBC). IEEE, 2017.

Tiwari, Pallavi, et al. "Multimodal wavelet embedding representation for data combination (MaWERiC): integrating magnetic resonance imaging and spectroscopy for prostate cancer detection." NMR in Biomedicine 25.4 (2012): 607-619.

Simonetti, Arjan W., et al. "Combination of feature-reduced MR spectroscopic and MR imaging data for improved brain tumor classification." NMR in Biomedicine: An International Journal Devoted to the Development and Application of Magnetic Resonance In vivo 18.1 (2005): 34-43.

Lemaitre, Guillaume, et al. "Computer-aided detection and diagnosis for prostate cancer based on mono and multi-parametric MRI: a review." Computers in biology and medicine 60 (2015): 8-31.

* cited by examiner

TUMOR TISSUE CHARACTERIZATION USING MULTI-PARAMETRIC MAGNETIC RESONANCE IMAGING

RELATED APPLICATION

The present patent document claims the benefit of the filing date under 35 U.S.C. § 119(e) of Provisional U.S. Patent Application Ser. No. 62/812,385, filed Mar. 1, 2019, which is hereby incorporated by reference.

FEDERALLY SPONSORED RESEARCH OR DEVELOPMENT

This invention was made with government support under CA172210 awarded by the National institutes of Health. The government has certain rights in the invention.

BACKGROUND

The present embodiments relate to magnetic resonance imaging (MRI). MRI is used for characterizing tissues, such as distinguishing between different types of tumor tissues. For example, tissue characterization of a brain tumor guides treatment due to delineation of the bulk neoplasm boundary and the extent and degree of neoplasm infiltration. For metastatic lesions, such as low- or high-grade gliomas, separation of the tissues as edema, necrotic, enhancing tumor, and cavity not only help monitor tumor progression but help choose preferred treatment and optimize targeting of tissue in case of resection or radiation.

MRI is used for tissue assessment. For brain tumor segmentation, generative models use prior information of the brain through atlas-based image registration to segment different types of tissues. However, the generative model relies on the quality of registration, which may be unreliable especially when the brain is deformed due to large tumors. Discriminative models segment brain tumors by classifying voxels based on image intensities. Structure information, such as from T1w, T1 post contrast, T2w, or fluid-attenuated inversion-recovery (Flair) parameters, are the most common MRI information to distinguish between tumor tissues. These four modalities or types of MRI structural information only provide basic structural features, which limits the information for discriminating different tumor tissues. Diffusion Tensor Imaging (DTI), such as ADC and TraceW, may be used to distinguish between tumor tissues.

SUMMARY

Systems, methods, and instructions on computer readable media are provided for characterizing tissue, such as classification and/or segmentation of brain tumor tissue from multi-parametric MRI. MRI spectroscopy, such as in combination with structural and/or diffusion MRI measurements, are used to classify. A machine-learned model or classifier distinguishes between the types of tissue in response to input of the multi-parametric MRI. To deal with limited training data for tumors, a patch-based system may be used. To better assist physicians in interpreting results, a confidence map may be generated using the machine-learned classifier.

In a first aspect, a method is provided for characterizing tumor tissue from multi-parametric imaging by a magnetic resonance (MR) scanner. The MR scanner scans a patient. The scanning includes structural, diffusion, and spectroscopy measurements of the patient. The tumor tissue of the patient is classified between two or more classes of tumor type. A machine-learned classifier classifies in response to input of the structural, diffusion, and spectroscopy measurements. An image of the tumor tissue segmented based on the two or more classes is displayed.

One or more types of structural, diffusion, and/or spectroscopy MRI parameters may be used. For example, the scan for the structural measurements includes two or more of T1, T2, FLAIR, and T1 Post-Contrast measurements. As another example, the scan for the diffusion measurements includes two or more of diffusion tensor imaging (DTI) axial diffusivity, DTI fractional anisotropy, DTI mean diffusivity, and diffusion weighted imaging (DWI) B0 measurements. In yet another example, the scan for the spectroscopy measurements includes two or more of N-acetyl aspartate, creatine, lactate, water, gix, inositol, and choline measurements.

In one embodiment, the classification is performed by the machine-learned classifier, where the machine-learned classifier is a fully connected neural network. Other types of neural networks, such as convolutional neural network (CNN), or machine-learned models may be used.

Rather than inputting the full image information, the classification may be by application of the machine-learned classifier patch-by-patch for different locations from the measurements. The machine-learned classifier may have been trained on training data of patches to create a greater number of training samples. In one approach, weighted sampling of normal tissue related to tumor tissue is used to avoid oversampling normal tissue. Alternatively, the full image information is input in application.

Different types of tissue may be distinguished (i.e., classified or segmented). In one approach, different types of tumor tissue include enhanced, edema, and cavity tumor types. Necrosis and/or a catch all "other" classes may be used. The classification may include more than the tumor tissue types, such as classifying between multiple tumor types and normal tissue.

Other information than the parameters may be input to the machine-learned classifier for classification. For example, a normal tissue mask or normal tissue masks are input.

In one embodiment, the input measurements for the different types of parameters are co-registered. For example, the structural, diffusion, and spectroscopy measurements of the patient are spatially registered prior to the input to the machine-learned classifier.

In another embodiment, the tumor tissue is located. The classification may then be directed at the tumor tissue and tissue adjacent to the tumor tissue. Tissues spaced from the adjacent tissue are not classified. Alternatively, all of the locations are classified.

In one embodiment, the tumor tissue is a brain tumor. The brain of a patient is scanned, and the classification is of brain tumor tissue.

In a further embodiment, an image processor generates a confidence map of the classifying. The confidence map is generated using drop-out in the machine-learned classifier. The displayed image includes the image of the tumor tissue and the confidence map.

The displayed image may include different classes at different locations, providing a segmentation. The classification by location provides a segmentation between different types of tissue.

In a second aspect, method is provided for training for segmentation in magnetic resonance imaging (MRI). Training data including multi-parametric MRI scans including spectroscopy and structural and/or diffusion and ground truth labeling of tumor tissues is acquired. A neural network is machine trained to classify tumor tissue based on the training data. The machine-trained neural network is stored for later application.

In one embodiment, the training data also includes normal tissue segmentation, such as between gray matter, white matter, and cerebrospinal fluid. Other types of data may be used.

The neural network may be a fully-connected neural network. Other networks, such as convolutional neural network, may be used. Various loss functions and regularization may be used, such as using a cross-entropy loss function with L2 regularization.

In a third aspect, a system is provided for segmentation of brain tissue in magnetic resonance imaging (MRI). An MRI scanner is configured to scan the brain tissue of a patient, the scan including MRI spectroscopy. An image processor is configured to segment between different types of the brain tissue by application of data from the scan in patches to a machine-learned model. The machine-learned model outputs the segmentation location-by-location based on the patches. A display is configured to display the segmentation of the brain tissue.

In one embodiment, the MRI scanner is configured to scan with the scan including MRI spectroscopy, MRI diffusion, and MRI structural. The image processor is configured to segment with the different types of the brain tissue being different types of tumor tissue.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Tissue characterization, such as brain tumor tissue characterization, uses multi-parametric MRI. Multi-parametric MR is used to determine the precise boundaries of different tumor tissues. The multi-parametric MRI scans are grouped into three categories: structural images, diffusion weighted images, and spectroscopy images. In order to gain precision in classification, brain MR spectroscopy, which quantifies presence of metabolites at the tumor location, is used to define active parts of the tumor. The multi-parametric MRI scans are used to identify brain tissue categories. These scans may offer added value in image interpretation, provide an alternative source of image contrast, and improve conspicuity to identify and potentially characterize pathology. This delineation may assist in diagnosis and neurosurgery. Compared to approaches that only use structural scans, the images features from diffusion weighted imaging and spectroscopy imaging may assist in more accurate segmentation.

In one embodiment, a neural network with dropout layers is used to create uncertainty for the classification. This uncertainty or confidence map indicates regions that have more ambiguity in discriminating tissue types. In practice, a semi-automatic pipeline may be provided for tissue characterization. The model prediction is used as a preliminary segmentation, and the confidence map assists radiologists to focus on ambiguous voxels.

Figure 1:
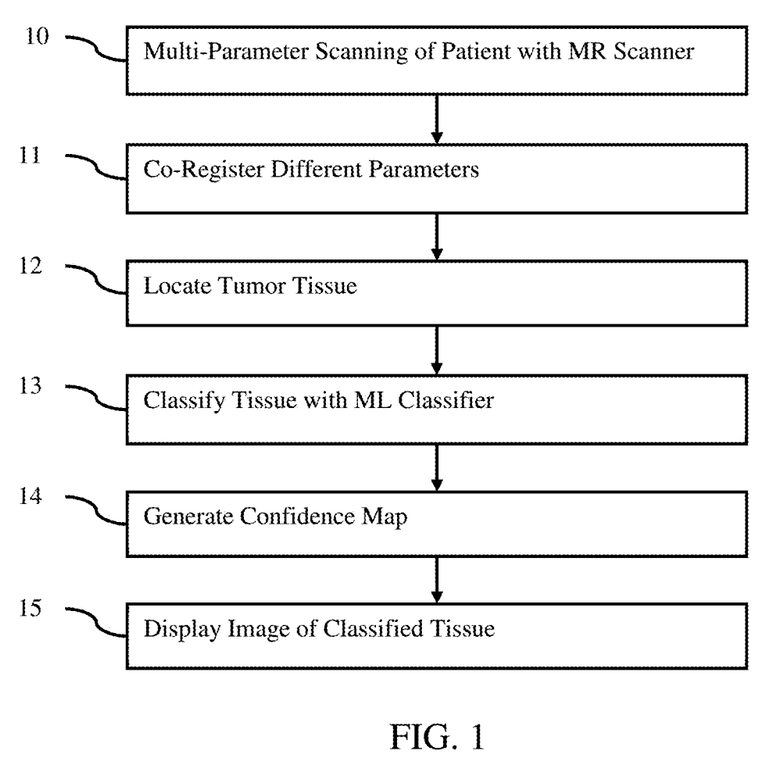
FIG. 1 is a flow chart of one embodiment of a method for characterizing tumor tissue from multi-parametric imaging by a magnetic resonance (MR) scanner.
Figure 2:
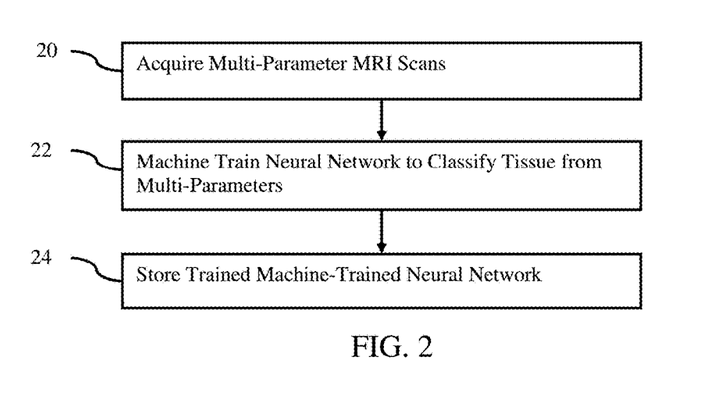
FIG. 2 is a flow chart of one embodiment of a method for training for segmentation in MRI.

FIG. 1 shows one embodiment of a method for characterizing tumor tissue from multi-parametric imaging by a MR scanner. The method is for application of a machine-learned classifier to distinguish between types of tissue, such as types of tumor tissue. MR spectroscopy with or without other types of parameters (e.g., diffusion and/or structural) is provided as input for a given patient. FIG. 2 is directed to training the classifier.

Figure 3:
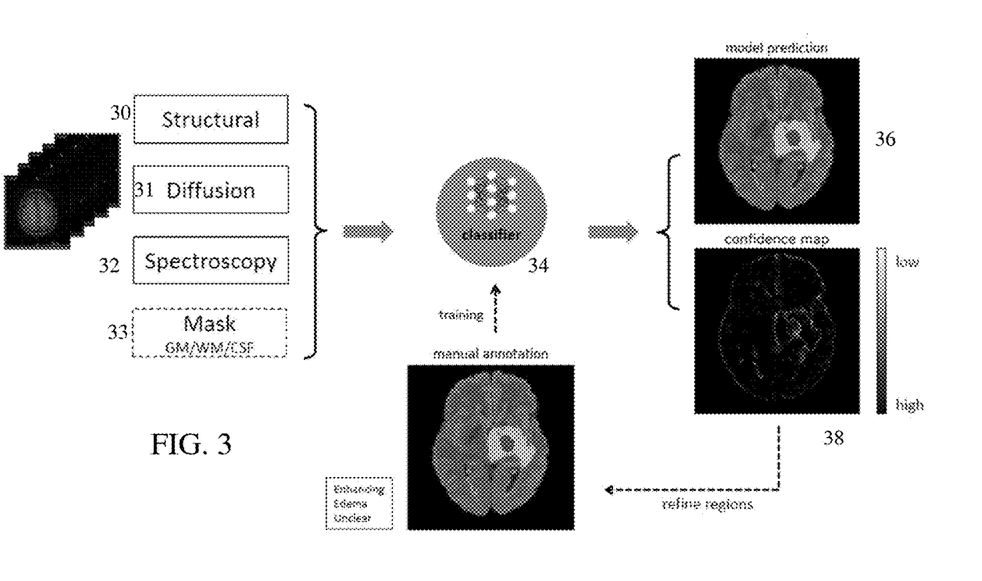
FIG. 3 illustrates an example diagram of tissue characterization.

FIG. 3 shows a schematic diagram for both training and application. Multi-parametric MRI scans 30-32, normal brain tissue segmentation 33, and manual labeling of tumor tissues 39 are used to train a classifier 34. In application, the multi-parametric scans 30-33 for a previously unknown patient with or without the normal brain tissue segmentation 33 are used as inputs to the trained classifier 34 to predict the tumor tissue labels 36. In application, a confidence map 38 of the tissue classification, which helps radiologists to refine the human delineation or make further diagnosis, may be generated by drop-out using the classifier 34.

Referring again to FIG. 1, the method is implemented by an image processor, such as part of a server, computer, or workstation. The image processor accesses previous scans, such as from a picture archiving and communications system, a computerized patient medical record, and/or transfer from an MR scanner. In another embodiment, the MR scanner acquires the data by scanning the patient, and an image processor of the MR scanner registers, locates, applies the machine-learned classifier, creates a confidence map, and generates an image. Other devices may be used.

The method is performed in the order shown (top to bottom or numerical). Other orders may be used. For example, act 12 is performed before act 11. As another example, act 15 is performed before act 14.

Additional, different, or fewer acts may be provided. For example, acts 11, 12, and/or 14 are not provided. As another example, acts for positioning the patient, generating MRI images, and/or assisting user diagnosis, tracing, and/or treatment planning are provided.

In act 10, the MR scanner scans a patient. The patient is positioned in the bore of the MR scanner and subjected to the B0 main magnetic field. MR pulses are transmitted in sequence with gradient magnetic fields. The responses are measured as k-space data. The scan data are measurements (e.g., k-space data or data reconstructed from the k-space data (e.g., reconstructed object domain)).

The scan is a volume scan, such as measuring for locations distributed along three dimensions. In alternative embodiments, a planar scan is performed.

The scan is of the brain of a patient. Alternatively, the scan is of the liver or other organ of the patient. The scan may be of the entire organ, multiple organs, and/or part of one or more organs. Brain tissue and brain tumor tissue examples are used herein, but other tissues and/or tumors may be scanned.

Multiple parameters are measured. Different scan patterns, including different pulse arrangements, may be used to acquire data representing different metrics. Any number of parameters of any number of categories may be used. In one embodiment, the multiple parameters include one or more structural parameters, one or more diffusion parameters, and/or one or more spectroscopy parameters. For example, two or more structural, two or more diffusion, and two or more spectroscopy measurements are acquitted. The scanning is performed sequentially. Alternatively or additionally, compressed sensing MR is used to acquire measurements for two or more parameters based on one scan pattern using MR fingerprinting.

Structural measurements measure the response from anatomy or tissue. Any of various structural measurements may be used. Example parameters include T1, T2, FLAIR, and T1 Post-Contrast measurements.

Diffusion measurements measure the response of fluid as a spatial distribution (how much water and/or distribution of water in a tissue) or a directional component of water distribution. Example diffusion measurements include diffusion tensor imaging (DTI), such as DTI axial diffusivity, DTI fractional anisotropy, and DTI mean diffusivity. Another example is diffusion weighted imaging (DWI), such as DWI B0 measurements.

Spectroscopy measurements measure response by particular molecules. Example spectroscopy measurements include N-acetyl aspartate (NAA), creatine, lactate, water, gix, inositol (e.g., myo-Inositol), glycine, acetate, alanine, glutamate, succinate, and choline measurements.

Other categories of MRI parameters may be used. For example, functional MR imaging may be used, such as measuring the uptake or operation of a body process. MR perfusion measurements using contrast-enhanced methods (DCE or DSC) may be used.

In one embodiment, multi-parametric MRI scans are used to identify brain tissue category by location. Each patient has multi-parametric MRI scans grouped into three categories: structural images, diffusion weighted images, and spectroscopy images. Table 1 shows four structural, four diffusion, and eleven spectroscopy scans and corresponding measurements used.

TABLE 1

List of multi-parametric MRI scans

| Category | Number of scans | List of scans |
| --- | --- | --- |
| Structural | 4 | T1, T2, FLAIR, T1 post-contrast |
| Diffusion | 4 | DTI_AD, DTI_FA, DTI_MD, DWI_B0 |
| Spectroscopy | 11 | NAcetylAspartate, tCreatine, Water_Sl, Glx, Glx_Sm, Lactate, Lactate_Sm, myo-Inositol, myo-Inositol_Sm, tCholine, tCholine_Sm |

Other parameters, number of categories, and/or number of parameters within a category may be used.

In act 11, the measurements from different times are co-registered. Where compressed sensing is used, the spatial alignment may already exist. Where sequential scans are performed, the resulting scan data in the object domain (e.g., after reconstruction or transform from k-space) is spatially aligned. The registration is a linear or affine registration or an elastic registration. Image intensity registration and/or features detection and registration are used.

In one embodiment, the MRI scans of the same patient are rigidly co-registered to a pre-contrast T1-weighted image scan. Before or after registration, the scan data is re-sampled at 1 mm isotropic resolution with a linear interpolator. Such alignment may instead be done by matching anatomical landmarks on all contrasts (e.g., in brain imaging—Bregma, crista galli, foragem magnum, left right orbits, falx). For brain imaging, bone anatomical landmarks give precise reference to realign contrasts back to T1w. After registration and re-sampling, the scans data may be z-score normalized based on the mean voxel intensity and standard deviation of the brain tissue region.

In act 12, an image processor locates the tumor tissue. Where the tissue to be classified is different classes of tumor tissue, the tumor is located. Where the tissue to be classified are different classes of normal tissue, the organ, organs, or tissue region with the different classes are located.

Any segmentation may be performed. The segmentation is a preprocessing step to later classify in act 13 within the located region with or without surrounding tissue. As the tumor region is just a subset of the full brain, one optional preprocessing step is to generate an approximate location or region of the tumor before proceeding to further tissue classification.

Figure 4:
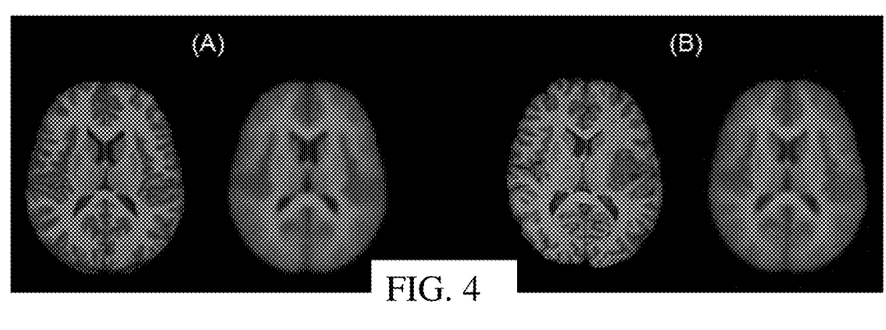
FIG. 4 shows example images for tumor localization.

Machine-learned models based on unsupervised learning from normal or control cases may be used. In one embodiment, a representation of normal brain distribution is learned to create a metric between a case (whether normal or with disease) and its normal representation. FIG. 4 shows an example where A is a T1 image (left) and VAE reconstruction (right) for normal brain and B is a T1 image (left) and VAE reconstruction (right) for a brain with a disease (e.g., tumor). The difference is used to locate the tumor. Such unsupervised learning may be done either via Variational AutoEncoders or a generative adversarial network (GAN)-like network, such as conditional GAN or Cycle GAN. The location may allow focusing the tissue characterization on and around this estimated region of the tumor. Other segmentation may be used. Alternatively, the classification is applied without preprocessing of the location of a region of interest.

In act 13, the image processor classifies the tumor tissue of the patient between two or more classes of tissue type, such as types of tumor tissue. For the brain tumor tissue example, the types may be enhanced, edema, cavity, necrosis, or other (e.g., unclear). In one example, enhanced, edema, and cavity are used without other or necrosis. The classes may include non-tumor tissue, such as normal tissue. More than one class of normal may be used, such as gray matter, white matter, and cerebrospinal fluid.

The classification is to be in response to input to the machine-learned classifier of the different or multi-parameters, such as in response to input of one or more of each of structural, diffusion, and spectroscopy measurements. Other information may additionally be input, such as information about a patient (e.g., diagnosis, genetic information, previous treatment, diet, and/or family history). In one embodiment, one or more masks or normal tissue are input. For example, the location of the tumor is used to generate a mask or segmentation of locations of normal tissue. As another example, different masks are provided for different types of normal tissue.

In one embodiment, a preprocessing step applies a different machine-learned model to form the masks. For example, deep learning is used to form a machine-learned model (e.g., neural network) for segmentation of masks. In one embodiment, a dual network is used for skull stripping segmentation, and a recursive neural network is used for normal tissue segmentation. The network outputs the locations or segmentation of gray matter (GM), white matter (WM) and cerebrospinal fluid (CSF). Hierarchal or separate machine-learned models may be used for identifying locations of the different types of normal tissue. Alternatively, manual segmentation or masking is used.

FIG. 3 shows an example of input of one or more structural measurements 30, one or more diffusion measurements 31, one or more spectroscopy measurements 32, and one or more normal tissue masks 33. The values of the measurements of different parameters are input to the classifier 34.

The classifier 34 is a fully connected neural network. This type of network allows for patches of any size to be used as inputs. Alternatively, such as for inputting full images or volumes or larger patches for a given application, a convolutional neural network may be used. Any network structure may be used. Any number of layers, nodes within layers, types of nodes (activations), types of layers, interconnections, learnable parameters, and/or other network architectures may be used.

The classifier 34 is a machine-learned classifier. Machine training uses the defined architecture, training data, and optimization to learn values of the learnable parameters of the architecture based on the samples and ground truth of the training data. FIG. 2 shows one embodiment of a method for training for segmentation in MRI. The training of FIG. 2 provides the machine-learned classifier 34 used in application for scan data of a previously unseen patient.

In act 20, training data is acquired and stored in a database or memory. The training data is acquired by aggregation, mining, loading from a publicly or privately formed collection, transfer, and/or access. Ten, hundreds, or thousands of samples of training data are acquired. The samples are from scans of different patients and/or phantoms. Simulation may be used to form the scan data.

The training data includes multi-parametric MRI scans. Each sample includes one or more structural scans, one or more diffusion scans, and/or one or more spectroscopy scans. For example, the four structural scans, four diffusion scans, and eleven spectroscopy scans of Table 1 are provided for each sample.

The training data may include other information. For example, preprocessing is used to provide masks and/or locate the tumor. Each sample includes one or more masks, such as masks for the organ or for specific structure in the organ. In one embodiment for brain imaging, masks are provided for the gray matter, white matter, and cerebrospinal fluid. The normal or healthy tissue of the brain is segmented. The segmentation may be by expert, automatically by an image processor, and/or semi-automatically where an image processor segments and a user refines. In one embodiment, a Dual Network is used for skull stripping, and recursive network or other deep learned neural network is used for the segmentation.

Patches may be used to increase the number of samples used for training. A given scan may represent an area or volume. The area or volume is sub-divided into overlapping or non-overlapping sub-sets—patches. Tens, hundreds, or thousands of patches may be formed for each scan. As a result, the number of training samples is increased as one scan sample may be used as many training samples. Alternatively, full scans are used as the training samples.

The training data includes ground truth data. Labels for the ground truth of each training sample are provided. For example, the tumor tissues are labeled. In the brain tumor tissue example, five different categories may be identified, such as manually identified, for abnormal tissues: edema, enhancing tumor, necrosis, cavity, and others (unclear category). In one embodiment, the types and locations of tumor tissue are identified by an expert from the structural and/or diffusional contrast scan data. Automatic or semi-automatic generation of the ground truth labels may be used. Other groups or classes of tumor tissue may be used, such as discriminating edema, enhancing tumor, cavity, and normal tissues.

In act 22, a machine (e.g., image processor, server, workstation, or computer) machine trains the neural network to classify tissues, such as different tumor tissues. The training uses the training data to learn values for the learnable parameters of the network. The training determines the values of the network that most consistently output close to or at the ground truth given the input sample. Any machine learning and corresponding network architecture may be used. For example, a neural network or support vector machine is used. The machine trains the network to output the class of a location or locations.

In one embodiment, the classifier 34 is trained based on 3D image patches either from the full brain or from the estimated or located tumor region (e.g., region including the tumor and adjacent normal tissue). Any size patch may be used, such as 3×3×3 $mm^3$ voxels to characterize the central voxel. The patch has the same label as the center voxel's label in the classification problem. The model is trained using patches to reduce the problem of lacking training samples. Thousands of patches may be extracted from scans for one patient. The size of the patches may vary or be larger or smaller to give more or less context about the brain region. Having bigger or multiple sizes around the center of a patch may be used.

All possible patches may be used. The patches may overlap so that one patch is provided per scan per voxel, or non-overlapping patches may be used. To save the time for training the model, not all patches of the patient are used for training. For each patient, a maximum number (e.g., 3000) of patches are randomly selected from each tumor tissue category or for the tumor regardless of category. All patches of the category are selected if the total number of patches is less than the maximum number. For the normal tissue, the same or different maximum number of patches adjacent to the tumor are selected. In one embodiment, an additional number (e.g., 3000) patches far from the tumor (i.e., spaced away from the adjacent healthy tissue) are also selected. Patches only for the tumor and adjacent to the tumor are used in other embodiments. In one embodiment, at most 15,000 patches per scan are selected for each patient. Given that the volumes of different tumor tissues may be different, the sample sizes of the categories may be imbalanced. A weighted sampling scheme may be used to reduce the training sample imbalance problem. During training, the probability of selecting a sample is assigned to be inversely proportional to the size (i.e., number of samples or patches) of its category in the training data.

Given the training data of the patches and corresponding ground truth labels, the network is trained. For example, a fully connected neural network with two hidden layers is used as the classifier. The input layer has 27*(N+3) nodes, where N is the number of image scans used for classification (e.g., N=19 in the example of table 1). The 27 value is the number of voxels in each patch. Three additional binary masks of normal tissues (gray matter, white matter, and cerebrospinal fluid) are input to corresponding nodes of the input layer. Other numbers of input nodes, hidden layers, and/or types of networks may be used.

Each hidden layer has 128 nodes with a dropout probability of 0.5. Other numbers of nodes, no drop out, and/or other probabilities of drop out may be used. Each node uses a rectified linear unit (ReLU) as non-linear activation function. Other activation functions may be used.

The output layer has 4 nodes to map the hidden feature vector to the desired number of classes (e.g., edema, enhanced, cavity, and normal). Additional or fewer output nodes may be used where there are other numbers of classes. The soft-max function is applied on the output to predict the probability of each category.

In training, the loss function is the cross entropy between prediction and ground truth. Other loss functions, such as L1 or L2, may be used. L2 regularization is applied on all network parameters (weight decay 10-5), but other or no regularization may be used. Adam with learning rate of 10-3 or other function is used for optimization. Other learning rates may be used.

Once trained, the machine-learned or trained neural network is stored in act 24. The training determines the values of the learnable parameters of the network. The network architecture, values of non-learnable parameters, and values of the learnable parameters are stored.

The machine-trained network is stored in memory. Copies may be distributed, such as to MR scanners, for application. Once stored, the machine-learned network may be fixed. The same machine-learned network may be applied to different patients.

The machine-learned network may be updated. As additional training data is acquired, such as through application of the network for patients and corrections by experts to that output, the additional training data 39 may be used to re-train or update the training of the classifier 34.

Returning to act 13 of FIG. 1 for application of a previously trained machine-learned network or other model, the previously unseen (by the classifier 34) scan data is input. The structural scan data 30, diffusion scan data 31, spectroscopy scan data 32, and/or mask(s) 33 for a patient are input to the classifier 34. The input may be patch-by-patch. The patches for a given voxel or location from all of the different MRI parameters and/or masks are input to the classifier 34 to classify for that voxel or location. Different patches are input to classify for different locations.

The classification may be performed for tumor tissue locations and locations adjacent to the tumor. The classification may not be performed for locations spaced from the adjacent tissue. Alternatively, the classification is performed for all locations. Random, regular, or other sampling of locations for classification may be performed.

In response to input, the classifier 34 outputs a classification for a given location. By repeating application for other locations, the classification for each of various locations is determined by the machine-learned network. For example, a spatial distribution of class is provided. FIG. 3 shows an example two-dimensional image of a plane where the class membership is used to generate an image. Different classes are mapped to different grayscale values, indicating spatial distribution amongst the different classes.

Further information to assist in diagnosis or planning may be provided. In one embodiment, the image processor generates a confidence map in act 14. The confidence in the classification outputs is determined using drop out in the machine-learned classifier. For each voxel or location, a confidence value is computed to indicate the consistency of the model prediction in multiple runs or applications of the classifier 34. The dropout layer or layers (e.g., two hidden layers) in the network are used to classify with the classifier 34 having different configurations. Classification is repeated with different network configurations. For each application, half of the nodes in the hidden layer and their corresponding connections to other nodes are randomly removed from the network. Other drop out probabilities may be used. A prediction for the volume (e.g., patch) is then calculated using the "modified" model (i.e., the altered model is applied to the input data). This random drop out process is repeated any number (e.g., 100) of times for each location, providing that number of different classification predictions for each voxel. The normalized entropy may be used to measure the uncertainty, n, of the prediction:

$$\eta = \frac{-\sum_{i=1}^{N} p(x_i) \log p(x_i)}{\log N}$$

where N is the number of possible categories, $x_i$ is the prediction for location i, and p is the normalized frequency of each category prediction. Note $\eta=1$ means complete randomness in the prediction and $\eta=0$ means the prediction is identical in all repetitions. Other confidence calculations, such as with different drop out settings, may be used (e.g., different numbers of nodes being dropped per repetition and/or different number of drop out configurations applied).

Figure 5:
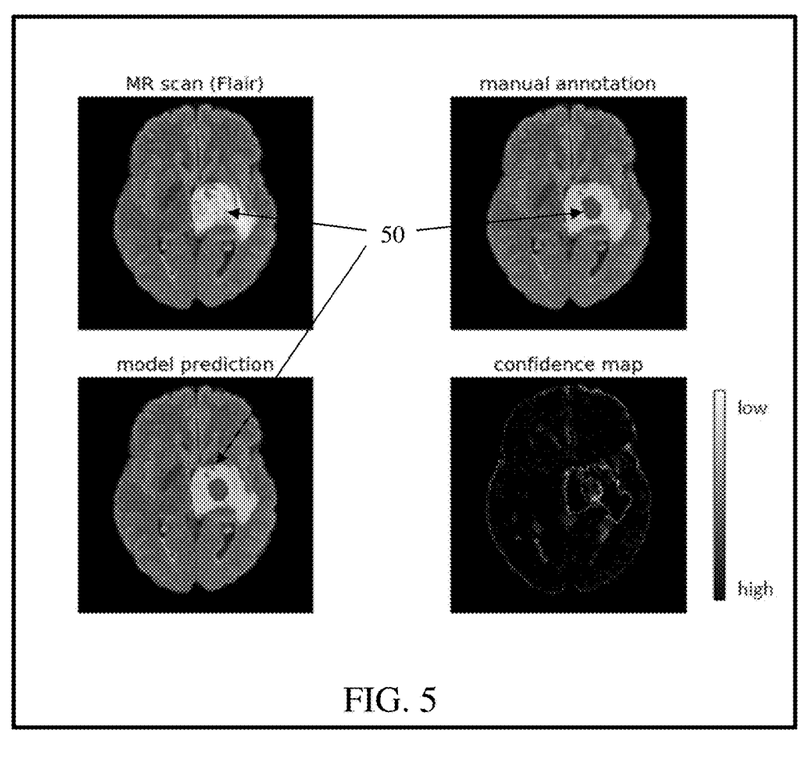
FIG. 5 shows example inputs and outputs for brain tumor classification.

FIG. 5 shows example images for an input MR scan (e.g., Flair), a manual annotation providing the ground truth, and a model prediction output after application to the classifier 34 to different voxels or locations. The tumor region 50 is visible in all three. These images are for a planar slice of a scan volume of the patient. A confidence map of this axial slice is also shown. In examining the confidence map, most of the ambiguous voxels are at the boundaries of manual annotations. This suggests that the confidence map may be used by experts to check annotations and refine the delineation of each tissue category.

In act 15, the image processor generates an image, which is displayed on a display device. The image is of the classified tissue, such as an image of tumor tissue. The distribution of class provides a segmentation. The image shows locations of tissue in two or more different classes. Each location is assigned a class. The class may be filtered, such as removing small contiguous regions.

Where voxels are classified, the image may be a two-dimensional or planar slice of the volume. Alternatively, three-dimensional rendering (e.g., volume rendering) is performed to provide a two-dimensional image for display.

The image may include other information. For example, the segmentation by class is used to generate a graphic or highlighting. An image from one or more of the MR parameters is generated. The graphics or highlighting from the classification is applied or overlaid on the MRI image. Alternatively, the segmentation is displayed without being an overlay.

In one embodiment, the image includes the classification of the tumor tissue and a confidence map. The confidence map is displayed separately from, such as adjacent to, the segmentation. Alternatively, the confidence is used to alter the segmentation, such as providing an overlay graphics or highlighting.

Performance of the machine-learned classifier may be tested. In one embodiment, training data is available for 57 patients. Training data for 45 patients is randomly selected for training of the classifier, and the performance testing of the trained classifier uses the training data from the remaining 12 patients.

In the testing phase, patches of the same size as the training data are used for all voxels within the brain region. The tissue type of the central voxel is predicted. Given that the testing data is dominated by normal voxels, the focus is on tissues surrounding the tumor region. Like the training data, 10,000 normal voxels distant from the tumor are selected and added to the testing set.

The Dice, Precision (or positive predictive value, PPV), and Sensitivity (or true positive rate, TPR) metrics are used to evaluate the model (i.e., machine-learned classifier). Each of the metrics is calculated on four kinds of tissues (i.e. edema, enhancing tumor, cavity and normal). The formulas of the three metrics are as follows:

$$Dice(Y, \overline{Y}) = \frac{|Y \cap \overline{Y}|}{(|Y| + |\overline{Y}|)/2}$$

$$PPV(Y, \overline{Y}) = \frac{|Y \cap \overline{Y}|}{|\overline{Y}|}$$

$$TPR(Y, \overline{Y}) = \frac{|Y \cap \overline{Y}|}{|Y|}$$

where Y denotes the true region of the tissue, $\overline{Y}$ denotes the predicted tissue region, $|Y \cap \overline{Y}|$ denotes the overlap area between ground truth and prediction, and $|Y|$ and $|\overline{Y}|$ denote the volumes of Y and $\overline{Y}$ respectively. The regions correspond to regions of the same class of tissue.

The classification performance may be evaluated using four different models based on inputs used. The input image scans to the models are 1) 4 structural images, 2) 4 structural images and 4 diffusion images, 3) 4 structural images and 11 spectroscopy images, 4) 4 structural images, 4 diffusion images and 11 spectroscopy images. Table 2 shows all three metrics of each tissue type separately. Both diffusion and spectroscopy images may improve the prediction accuracy. Combining all three types of image modalities yields the best performance.

TABLE 2

Tissue classification performance using different image modalities

| | Structures | | | Strectural + Diffusion | | | Structural + Spectroscopy | | | Structural + Diffusion + Spectroscopy | | |
|---|---|---|---|---|---|---|---|---|---|---|---|---|
| | Dice | PPV | TPR | Dice | PPV | TPR | Dice | PPV | TPR | Dice | PPV | TPR |
| Normal (12) | 0.91 | 0.93 | 0.68 | 0.92 | 0.92 | 0.92 | 0.91 | 0.89 | 0.94 | 0.92 | 0.89 | 0.95 |
| Edema (12) | 0.78 | 0.87 | 0.72 | 0.79 | 0.89 | 0.72 | 0.83 | 0.90 | 0.78 | 0.84 | 0.91 | 0.78 |
| Enhancing tumor (9) | 0.51 | 0.41 | 0.31 | 0.55 | 0.47 | 0.91 | 0.53 | 0.43 | 0.89 | 0.54 | 0.46 | 0.89 |
| Cavity (2) | 0.60 | 0.50 | 0.77 | 0.66 | 0.68 | 0.65 | 0.61 | 0.65 | 0.64 | 0.58 | 0.84 | 0.45 |
| Overall Accuracy | | 0.844 | | | 0.872 | | | 0.873 | | | 0.890 | |

PPV: positive predictive value or precision;
TPR: true positive rate or sensitivity
The number in the parenthesis indicates the number of patients with this tissue type in the manual annotation.

To further evaluate the model performance, the whole 3D volume of a patient may be segmented in the testing dataset by predicting the category of each voxel. The segmentation results are post-processed by removing all 3D-connected regions smaller than 100 mm$^3$. Table 3 shows the confusion matrix of the prediction using all 19 image modalities (multi-parameters of Table 1) on one patient. Voxels with unclear manual tissue labels (i.e. other) are grouped into the normal or one of the abnormal tissue categories.

TABLE 3

Confusion matrix of whole volume prediction (one sample patient)

| | | Prediciton label | | | | | |
|---|---|---|---|---|---|---|---|
| | | Normal | Edema | Enhancing | Necrosis | Cavity | Other | Sensitivity |
| True label | Normal | 1406376 | 1044 | 387 | 0 | 14602 | 0 | 0.99 |
| | Edema | 4541 | 51008 | 605 | 0 | 0 | 0 | 0.91 |
| | Enhancing | 1 | 37 | 3945 | 0 | 0 | 0 | 0.99 |
| | Necrosis | 0 | 0 | 0 | 0 | 0 | 0 | — |
| | Cavity | 0 | 0 | 0 | 0 | 0 | 0 | — |
| | Other | 104 | 932 | 1688 | 0 | 0 | 0 | — |

The confusion matrix gives insight not only into the overall errors being made by the model (i.e. accuracy of each tissue type) but more importantly the specific types of errors that are being made. For example, in Table 3, about 9% of Edema voxels are predicted as normal, so a radiologist might want to have a further check on those voxels to confirm whether the model categorized in error or there is an original annotation error. Sometimes the error may be neglected if located in a region that is less important. The confusion matrix may be output for radiologist review. Alternatively, the confusion matrix is used during development or training and not provided for a particular radiologist and/or patient.

Figure 6:
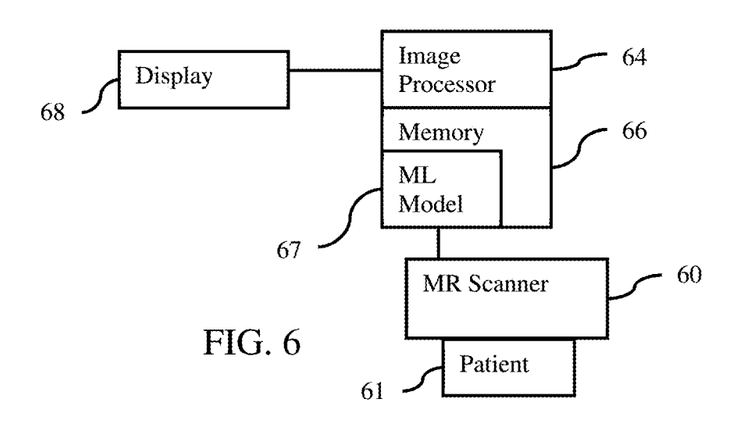
FIG. 6 is a block diagram of one embodiment of a system for segmentation of brain tissue in MRI.

FIG. 6 is a block diagram of a medical imaging system for segmentation of brain tissue in MRI. The system is for application of a machine-learned model 67 and/or for training of the machine-learned model 67. Multiparameter MRI is used to better classify tissue types, such as type of brain tumor tissue.

The medical imaging system includes the display 68, memory 66, and image processor 64. The display 68, image processor 64, and memory 66 may be part of the MR scanner 60, a computer, server, or another system for image processing to segment. A workstation or computer without the MR scanner 60 may be used as the medical imaging system. Additional, different, or fewer components may be provided, such as including a computer network for communication.

The MR scanner 60 is a medical diagnostic imaging system configured to scan a volume of a patient for each of multiple MR parameters. A main magnet or coil generates a substantially uniform magnetic field through the patient 61. Gradient coils, local coils, and/or a whole-body coil generate a pulse sequence to shift spin axes of molecules in the patient away from the uniform magnetic field lines. The local coils and/or whole-body coil detect radio frequency emissions caused by the relaxation of the spin axes of the molecules returning to the magnetic field lines. This k-space data is reconstructed into an object or spatial domain using Fourier processing. After transform, the scan or image data represents tissue response from a region of the patient 61.

The pulse sequences are performed for different of the MRI parameters. Measurements are obtained for one or more structural, one or more diffusion, and/or one or more spectroscopy parameters. The MR scanner 60 is configured, by settings, to scan the tissue of the patient. For example, a user selects an application for brain tissue or brain tumor scanning. The MR scanner 60 is configured to perform measurements for any number of different parameters, such as the 19 parameters listed in table 1.

The image processor 64 is a control processor, general processor, digital signal processor, three-dimensional data processor, graphics processing unit, application specific integrated circuit, field programmable gate array, artificial intelligence processor, digital circuit, analog circuit, combinations thereof, or another now known or later developed device for segmenting or classifying. The image processor 64 is a single device, a plurality of devices, or a network. For more than one device, parallel or sequential division of processing may be used. Different devices making up the image processor 64 may perform different functions. In one embodiment, the image processor 64 is a control processor or other processor of a medical diagnostic imaging system, such as the MR scanner 60. The image processor 64 operates pursuant to stored instructions, hardware, and/or firmware to perform various acts described herein, such as registering, locating, classifying, and generating of the confidence map.

In one embodiment, the image processor 64 is configured to segment between different types of the brain tissue. The segmentation is performed by application of scan data from the scans in patches to the machine-learned model 67. The model 67 is applied for different voxels or locations by input of the corresponding patches. The segmentation is generated by output of the classification location-by-location based on the patches. For example, the locations of different types of brain tissue and/or brain tumor tissue are output.

The image processor 64 is configured to output one or more images showing spatial distribution of the classification. Images from one or more the MRI parameters may also be output. A confidence map for the classification may be output. The classification or segmentation may be post-processed, such as spatially filtered or mapped to annotations or graphics. The information from the post processing is used to generate an image.

The display 68 is a CRT, LCD, projector, plasma, printer, tablet, smart phone or other now known or later developed display device. The display 68 displays the segmentation image as part of, with, or separately from other MR images for the patient. An image for the confidence map may be displayed. The display 68 displays images for diagnosis, prognosis, and/or treatment planning.

The instructions, ground truths, scan data, registration, tumor location, machine-learned network, outputs, confidence map, segmentation, and/or other information are stored in a non-transitory computer readable memory, such as the memory 66. The memory 66 is an external storage device, RAM, ROM, database, and/or a local memory (e.g., solid state drive or hard drive). The same or different non-transitory computer readable media may be used for the instructions and other data. The memory 66 may be implemented using a database management system (DBMS) and residing on a memory, such as a hard disk, RAM, or removable media. Alternatively, the memory 66 is internal to the processor 64 (e.g. cache).

The instructions for implementing the processes, methods, and/or techniques discussed herein are provided on non-transitory computer-readable storage media or memories, such as a cache, buffer, RAM, removable media, hard drive or other computer readable storage media (e.g., the memory 66). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for characterizing tumor tissue from multi-parametric imaging by a magnetic resonance (MR) scanner, the method comprising:
    scanning a patient by the MR scanner, the scanning including structural, diffusion, and spectroscopy measurements of the patient;
    classifying the tumor tissue of the patient between two or more classes of tumor type, the classifying by a machine-learned neural network in response to input of the structural, diffusion, and spectroscopy measurements;
    generating a confidence map comprising confidence values for each voxel that indicate a consistency of the machine-learned neural network's classification predictions over different network configurations; and
    displaying an image of the tumor tissue segmented based on the two or more classes and the confidence map.

2. The method of claim 1 wherein scanning comprises scanning with the structural measurements including two or more of T1, T2, FLAIR, and T1 Post-Contrast measurements.

3. The method of claim 1 wherein scanning comprises scanning with the diffusion measurements including two or more of diffusion tensor imaging (DTI) axial diffusivity, DTI fractional anisotropy, DTI mean diffusivity, and diffusion weighted imaging (DWI) B0 measurements.

4. The method of claim 1 wherein scanning comprises scanning with the spectroscopy measurements including two or more of N-acetyl aspartate, creatine, lactate, water, gix, inositol, and choline measurements.

5. The method of claim 1 wherein the machine-learned neural network comprises a fully connected neural network.

6. The method of claim 1 wherein classifying comprises classifying by application of the machine-learned neural network patch-by-patch for different locations from the measurements.

7. The method of claim 1 wherein classifying comprises classifying as enhanced, edema, necrosis, and cavity tumor types.

8. The method of claim 1 wherein classifying comprises classifying between the two or more classes of tumor type and a class of normal tissue.

9. The method of claim 1 wherein classifying comprises classifying by the machine-learned neural network in response to input of the structural, diffusion, and spectroscopy measurements and a normal tissue mask.

10. The method of claim 1 further comprising co-registering the structural, diffusion, and spectroscopy measurements of the patient prior to the input to the machine-learned neural network.

11. The method of claim 1 further comprising locating the tumor tissue, wherein classifying comprises classifying the tumor tissue and tissue adjacent the tumor tissue without classifying tissue located a predetermined number of patches from the tissue adjacent the tumor tissue.

12. The method of claim 1 wherein scanning comprises scanning a brain of the patient, and wherein classifying comprises classifying the tumor tissue as brain tumor tissue.

13. The method of claim 1 wherein the machine-learned neural network was trained on training data of patches using weighted sampling of normal tissue related to tumor tissue.

14. The method of claim 1, wherein for the different network configurations half of the nodes in a hidden layer and their corresponding connections to other nodes are randomly removed from the machine-learned neural network.

* * * * *